United States Patent [19]

Hauck et al.

[11] 4,093,814

[45] June 6, 1978

[54] ESTERS OF 4-[3-(SUBSTITUTED AMINO)-2-HYDROXYPROPOXY]-5,6,7,8-TETRAHYDRO-1,6,7-NAPHTHALENETRIOLS

[75] Inventors: Frederic P. Hauck, Somerville; Michael E. Condon, Lawrenceville; Rita T. Fox, Princeton, all of N.J.

[73] Assignee: E. R. Squibb & Sons, Inc., Princeton, N.J.

[21] Appl. No.: 798,275

[22] Filed: May 18, 1977

Related U.S. Application Data

[62] Division of Ser. No. 656,769, Feb. 9, 1976, Pat. No. 4,048,231.

[51] Int. Cl.² .................. C07G 93/06; C07C 93/26
[52] U.S. Cl. .................... 560/139; 560/20; 560/22; 560/55; 560/73; 560/105; 560/108
[58] Field of Search ............ 560/139, 108, 55, 73, 560/20, 22, 105

[56] References Cited

U.S. PATENT DOCUMENTS 3,935,267   1/1976   Hauck et al. .................. 560/139

*Primary Examiner*—Jane S. Myers
*Attorney, Agent, or Firm*—Lawrence S. Levinson; Merle J. Smith; Donald J. Barrack

[57] ABSTRACT

Compounds having the formula

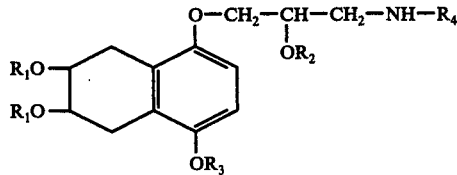

wherein $R_1$, $R_2$ and $R_3$ are hydrogen or acyl, and $R_4$ is lower alkyl have utility in the treatment of coronary diseases.

10 Claims, No Drawings

ESTERS OF 4-[3-(SUBSTITUTED AMINO)-2-HYDROXYPROPOXY]-5,6,7,8-TETRAHYDRO-1,6,7-NAPHTHALENETRIOLS

This is a division of copending application Ser. No. 656,769 now U.S. Pat. No. 4,048,231, filed Feb. 9, 1976.

SUMMARY OF THE INVENTION

Compounds having the formula

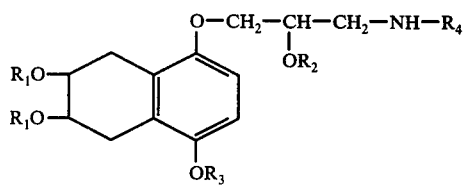

are useful in the treatment of coronary diseases. In formula I, and throughout the specification, the symbols are as defined below.

$R_1$, $R_2$ and $R_3$ are the same or different and are hydrogen or acyl, with the proviso that if they are acyl, they are the same acyl group; and $R_4$ is lower alkyl.

The term "acyl", as used throughout the specification, refers to groups having the formula

wherein X can be a straight or branched chain alkyl group having 1 to 11 carbon atoms, an aryl group, or an aryl-lower alkyl. Exemplary acyl groups are acetyl, propionyl, butyryl, isobutyryl, hexanoyl, heptanoyl, decanoyl, dodecanoyl, benzoyl, o-tolyl, p-nitrobenzoyl, phenylacetyl, 3-phenylpropionyl, 3-(p-chlorophenyl)-butanoyl, and the like.

The term "lower alkyl" as used throughout the specification, includes both straight and branched chain alkyl groups having 1 to 8 carbon atoms; lower alkyl groups having 1 to 4 carbon atoms are preferred.

The term "lower alkoxy", as used throughout the specification, refers to groups having the formula YO— wherein Y is lower alkyl as defined above.

The term "aryl", as used throughout the specification, refers to phenyl and phenyl substituted with one or two lower alkyl, lower alkoxy, halogen, or nitro groups.

The term "aryl-lower alkyl", as used throughout the specification, refers to a lower alkyl group (as defined above) substituted with an aryl group (as defined above).

The term "halogen", as used throughout the specification, refers to fluorine, chlorine, bromine, and iodine.

DETAILED DESCRIPTION OF THE INVENTION

The compounds of formula I, and the pharmaceutically acceptable salts thereof, are useful as antifibrillatory agents and can be used to arrest cardiac arrhythmia in mammals by the inhibition of beta adrenergic receptors in the myocardium. For this purpose a compound of formula I, or a pharmaceutically acceptable salt thereof, may be incorporated in a conventional dosage form such as a tablet, capsule, elixir, injectable or the like, along with the necessary carrier material, excipient, lubricant, buffer, or the like. Daily doses of from about 5 to 100 milligrams per kilogram of body weight, preferably about 5 to 10 milligrams per kilogram of body weight can be administered in single or divided doses as described above.

The compounds of formula I can be prepared using as a starting material 1,4-diacetoxy-5,8-dihydronaphthalene, i.e., the compound having the formula

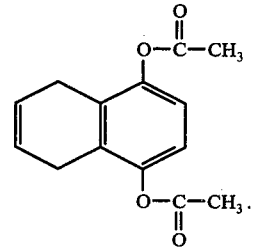

1,4-Diacetoxy-5,8-dihydronaphthalene is a known compound; see, for example, Chem. Ber., 62:2345 (1929).

The compounds of formula I include compounds wherein the $R_1O$- groups are in the cis and the trans configurations. The configuration of the final product is determined by the initial reaction of 1,4-diacetoxy-5,8-dihydronaphthalene to yield 1,4,6,7-tetrahydroxy-5,6,7,8-tetrahydronaphthalene having the formula

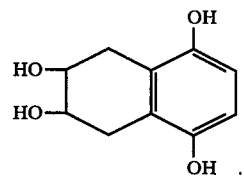

trans-1,4,6,7-Tetrahydroxy-5,6,7,8-tetrahydronaphthalene can be prepared from the diacetate of formula II by dissolving the diacetate in acetic acid, and then treating the solution with from about 2 to about 4 equivalents of silver acetate and from about 1 to about 2 equivalents of iodine. The mixture is then heated at a temperature of from about 80° to about 120° C for a period of from about 1 to about 24 hours under nitrogen, to yield the compound of formula III wherein the 6 and 7 hydroxy groups are in the trans configuration.

cis-1,4,6,7-Tetrahydroxy-5,6,7,8-tetrahydronaphthalene can be prepared from the diacetate of formula II by dissolving the diacetate in acetic acid and water (from 92 to 98% acetic acid, preferably 96% acetic acid), and then treating the solution with silver acetate and iodine and heating at a temperature of from about 80° to 120° C for a period of from about 1 to about 24 hours under nitrogen.

Prior to alkylating one of the phenolic hydroxy groups of a 1,4,6,7-tetrahydroxy-5,6,7,8-tetrahydronaphthalene of formula III, it is necessary to first protect the adjacent hydroxy groups attached to the nonaromatic ring. This can be accomplished as described in U.S. Pat. No. 3,856,818 issued Dec. 24, 1974. The resulting tetrahydronaphthalene has the formula

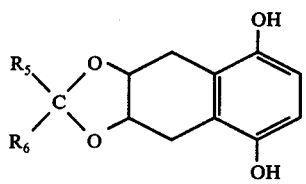

wherein $R_5$ and $R_6$ are each hydrogen, lower alkyl or aryl.

Alkylation of a compound of formula IV with epichlorohydrin yields a compound having the formula

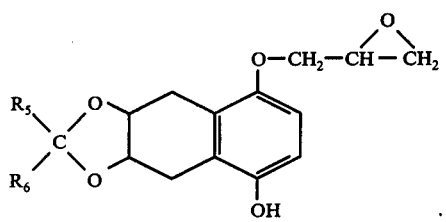

The reaction can be run by forming a mixture of a blocked tetrahydronaphthalenediol of formula IV and epichlorohydrin in an organic solvent such as acetone and heating the mixture in an inert atmosphere. While heating, an alkali such as sodium hydroxide is added to the mixture. The compounds of formula V are novel intermediates, and as such they constitute a part of this invention.

To prepare a compound of formula I wherein $R_1$, $R_2$ and $R_3$ are each hydrogen, an oxirane compound of formula V is reacted with an alkylamine having the formula $$H_2N-R_4 \qquad VI$$

to form an amine having the formula

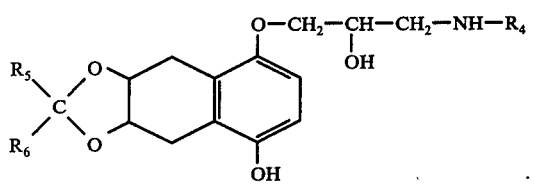

The reaction can be run in an organic solvent and is most conveniently run at ambient tamperatures. Acid hydrolysis of a compound of formula VII yields the product of formula I wherein $R_1$, $R_2$ and $R_3$ are each hydrogen, i.e., a compound having the formula

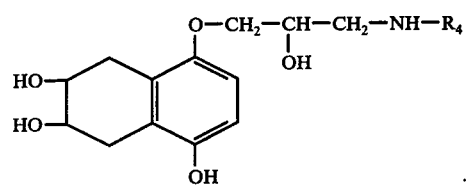

The compounds of formula VII are novel intermediates that constitute a part of this invention. Additionally, the compound possesses useful pharmacological activity, and can be used to arrest cardiac arrhythmia in mammals by the inhibition of beta adrenergic receptors in the myocardium.

The products of formula I wherein $R_1$, $R_2$ and $R_3$ are each acyl can be prepared by first converting an amine of formula VIII to an acid-addition salt to prevent acylation of the amino group. The acid-addition salt is then acylated using conventional techniques, e.g., reaction with an appropriate acid anhydride or acid chloride.

The products of formula I wherein $R_1$ and $R_2$ are hydrogen and $R_3$ is acyl can be prepared from the corresponding compound of formula VII. Before proceeding with the acylation reaction it is necessary to protect the hydroxy group in the aminopropoxy side chain of the compound of formula VII. Various means for protecting the hydroxy group will be apparent to the practitioner of this invention. An exemplary method comprises reacting a compound of formula VII with an aldehyde having the formula $$R_7CHO, \qquad IX$$

wherein $R_7$ is lower alkyl or aryl, to yield an oxazolidine derivative having the formula

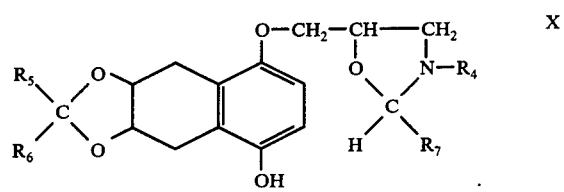

The reaction can be run in an organic solvent, preferably at the reflux temperature of the solvent. An oxazolidine derivative of formula X can be acylated with an acid anhydride or acid chloride to yield a compound having the formula

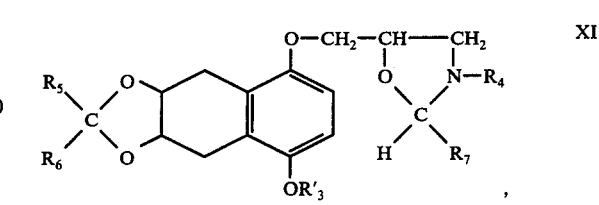

wherein $R'_3$ is acyl. Hydrolysis of a compound of formula XI yields a product of formula I wherein $R_1$ and $R_2$ are hydrogen and $R_3$ is acyl.

The products of formula I wherein $R_1$ is hydrogen and $R_2$ and $R_3$ are acyl can be prepared from a compound of formula V. Reaction of a compound of formula V with a secondary amine having the formula $$H-NR_4R_8, \qquad XII$$

wherein $R_8$ is aryl-lower alkyl, yields a compound having the formula

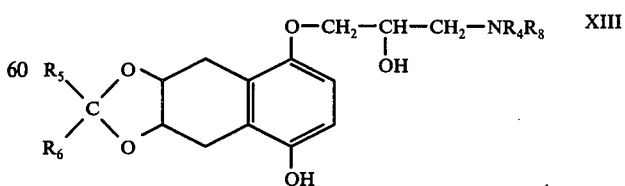

The compound of formula XIII can be acylated with an acid anhydride or acid chloride to yield a compound having the formula

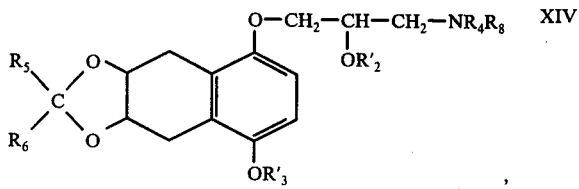

wherein $R'_2$ and $R'_3$ are acyl. Hydrolysis of a compound of formula XIV yields a compound having the formula

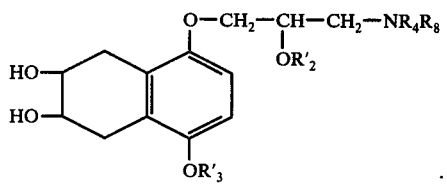

Reduction of a compound of formula XV, e.g., with gaseous hydrogen over a catalyst such as palladium, yields the corresponding product of formula I wherein $R_1$ is hydrogen and $R_2$ and $R_3$ are acyl.

The compounds of formula I form acid-addition salts with inorganic and organic acids. These acid-addition salts frequently provide useful means for isolating the products from reaction mixtures by forming the salt in a medium in which it is insoluble, and then neutralizing the salt with a base such as sodium hydroxide to obtain the free base. Any other salt may then be formed from the free base and the appropriate inorganic or organic acid. Illustrative are the hydrohalides, especially the hydrochloride and hydrobromide which are preferred, sulfate, nitrate, phosphate, borate, acetate, oxalate, tartrate, maleate, citrate, succinate, benzoate, ascorbate, salicyclate, methanesulfonate, benzenesulfonate, toluenesulfonate, and the like.

The following examples are specific embodiments of this invention.

EXAMPLE 1

8-[3-[(1,1-Dimethylethyl)amino]-2-hydroxypropoxy]-3a,9a-cis-3a,4,9,9a-tetrahydro-2,2-dimethylnaphtho[2,3-d]-1,3-dioxol-5-ol (a) 1,4,6,7-Tetrahydroxy-5,6,7,8-tetrahydronaphthalene To a solution of 89.2 g of 1,4-diacetoxy-5,8-dihydronaphthalene in 1.8 liters of glacial acetic acid and 72 ml of water is added 106.6 g of silver acetate followed by 81.2 g of iodine. The resulting slurry is then heated with stirring at 85° C ± 10° C for 3 hours under nitrogen. The reaction mixture is then cooled, filtered, and the filtrate concentrated in vacuo.

To a solution of the above residue in 1 liter of methanol at 0° C is added a solution of 160 g of sodium hydroxide in 800 ml of water, and the resulting mixture is stirred at room temperature overnight. Most of the methanol is then removed in vacuo, the resulting aqueous solution is chilled, acidified with cold concentrated hydrochloric acid, and this solution is thoroughly extracted with n-butanol. The combined extracts are washed with saturated aqueous sodium chloride and concentrated to near dryness in vacuo. The resulting precipitate is filtered and washed well with ether to give 20 g of the title compound, melting point 221°–224° C.

(b) 5,8-Dihydroxy-3a,9a-cis-3a,4,9,9a-tetrahydro-2,2-dimethylnaphtho[2,3-d]-1,3-dioxole A slurry of 19.6 g (0.10 mole) of 1,4,6,7-tetrahydroxy-5,6,7,8-tetrahydronaphthalene in 250 ml of 2,2-dimethoxypropane is stirred in the presence of a trace of p-toluenesulfonic acid. Within 15 minutes almost all solid has dissolved. After 1 hour the solution is diluted with an equal volume of ether, the resulting solution filtered through Celite to remove a small amount of suspended matter, the filtrate washed with dilute aqueous sodium bicarbonate, dried, and concentrated in vacuo to 18 g of crystalline product.

(c) 8-[2,3-(Epoxy)propoxy]-3a,9a-cis-3a,4,9,9a-tetrahydro-2,2-dimethylnaphtho[2,3-d]-1,3-dioxol-5-ol A stirred mixture of 18 g of 5,8 dihydroxy-3a,9a-cis-3a,4,9,9a-tetrahydro-2,2-dimethylnapththo[2,3-d]-1,3-dioxole, 60 ml of epichlorohydrin, 60 ml of acetone and 10 ml of water is heated to reflux under nitrogen. A solution of 3.2 g of sodium hydroxide in 20 ml of water is then added over 15 minutes. After the addition is complete, the mixture is refluxed for an additional 45 minutes.

The reaction mixture is then concentrated in vacuo (care is exercised to remove all excess epichlorohydrin to avoid further alkylation during base extraction), and the residue is partitioned between water and chloroform. The aqueous layer is extracted with chloroform, and the combined chloroform extracts washed with saturated aqueous sodium chloride, dired, and concentrated in vacuo to yield 28.8 g of oil.

The oil is combined with a previously prepared sample 6.1 g, (total=34.9 g), dissolved in ethyl acetate, and thoroughly extracted with cold dilute aqueous sodium hydroxide. The combined aqueous extracts are chilled, acidified with cold dilute aqueous acetic acid and the resulting solution is thoroughly extracted with ethyl acetate. The combined organic extracts are dried and concentrated in vacuo to 11.5 g of oil. The oil is taken up in chloroform and applied to an alumina column (300 g, Activity III, neutral). Fractions 1–3 (250 ml) consist of non-polar material. Fractions 3–10 (250 ml) give 3.1 g of the title compound after concentration in vacuo, and trituration with hexane/isopropyl ether.

(d) 8-[3-[(1,1-Dimethylethyl)amino]-2-hydroxypropoxy]-3a,9a-cis-3a,4,9,9a-tetrahydro-2,2-dimethylnaphtho[2,3-d]-1,3dioxol-5-ol A solution of 3.1 g of 8-[2,3-(epoxy)propoxy]-3a,9a-cis-3a,4,9,9a-tetrahydro-2,2-dimethylnaphtho[2,3-d]-1,3-dioxol-5-ol in 40 ml of absolute ethanol, 30 ml of benzene and 20 ml of t-butylamine is left overnight at room temperature. The solvents are removed in vacuo to yield the title compound.

EXAMPLE 2 cis-4-[3-[(1,1-Dimethylethyl)amino]-2-hydroxypropoxy]5,6,7,8-tetrahydro-1,6,7-naphthalenetriol, hydrochloride (1:1)

8-[3-[(1,1-Dimethylethyl)amino]-2-hydroxypropoxy]-3a,9a-cis-3a,4,9,9a-tetrahydro-2,2-dimethylnaphtho[2,3-d]-1,3-dioxol-5-ol, prepared above in Example 1, is dissolved in 100 ml of 5% hydrochloric acid and left at room temperature for 1 hour. This solution is then concentrated in vacuo to a foam. This is dissolved in hot isopropanol, decolorized with Norite, and diluted with ether. The resulting precipitate is subjected to the same treatment to give 1.2 g of amorphous solid. The amorphous material (1.2 g) is then recrystallized from isopro-

EXAMPLE 3 cis-4-[2-(Acetyloxy)-3-[(1,1-dimethylethyl)amino]-propoxy]-5,6,7,8-tetrahydro-1,6,7-naphthalenetriol, triacetate ester, hydrochloride (1:1)

cis-4-[3-[(1,1-Dimethylethyl)amino]-2-hydroxypropoxy]-5,6,7,8-tetrahydro-1,6,7-naphthalenetriol hydrochloride (1:1)(3.62g) is added to 50 ml of trifluoroacetic acid and the resulting solution is stirred at 0°–5° C while adding 6.4 ml of acetyl chloride dropwise. After the addition is completed, the solution is allowed to stand at room temperature for 1 hour. The solution is then concentrated in vacuo, the residue diluted with aqueous sodium bicarbonate, and then extracted with ethyl acetate. The ethyl acetate extracts are washed with saturated aqueous sodium chloride, dried, and concentrated in vacuo. The residue is dissolved in dry ether, chilled, and treated with hydrogen chloride saturated isopropanol. The resulting precipitate is filtered and recrystallized to yield the title compound.

EXAMPLE 4 cis-4-[3-[(1,1-Dimethylethyl)amino]-2-hydroxypropoxy]-5,6,7,8-tetrahydro-1,6,7-naphthalenetriol, 1-acetate A solution of cis-8-[3-[(1,1-Dimethylethyl)amino]-2-hydroxypropoxy]-3a,4,9,9a-tetrahydro-2,2-dimethylnaphtho[2,3-d]-1,3-dioxol-5-ol (7.31 g) and benzaldehyde (5.3g) in 100 ml of xylene is refluxed for 48 hours with constant separation of water (Dean-Stark trap). The xylene and most of the excess benzaldehyde is removed in vacuo, the residue taken up in a mixture of pyridine (70 ml) and acetic anhydride (30 ml), and this solution left at room temperature for 16 hours. The pyridine and excess acetic anhydride are removed in vacuo, the residue taken up in a cold (0° C) mixture of 225 ml of 5% hydrochloric acid and 25 ml of methanol, and the reaction mixture is stirred at 0°–5° C for 2 hours. Most of the methanol is removed in vacuo and the solution is made basic with 5% aqueous sodium bicarbonate and extracted with ether. The combined extracts are dried over magnesium sulfate and concentrated in vacuo to yield the title compound.

EXAMPLE 5 cis-4-[2-(Acetyloxy)-3-[(1,1-Dimethylethyl)amino]-propoxy]-5,6,7,8-tetrahydro-1,6,7-naphthalenetriol, 1-acetate A solution of 6.2g of cis-8-[2,3-(epoxy)propoxy]-3a,4,9,9a-tetrahydro-2,2-dimethylnaphtho[2,3-d]-1,3-dioxol-5-ol in 80 ml of absolute ethanol, 60 ml of benzene, and 20 ml of benzyl t-butylamine is left at room temperature for 16 hours. The solution is taken to dryness in vacuo, the residue taken up in 70 ml of pyridine and 30 ml of acetic anhydride, and this solution is allowed to stand at room temperature for 16 hours. The solution is then taken to dryness in vacuo, a cold (6° C) mixture of 225 ml of 5% hydrochloric acid and 25 ml of methanol is added, and the mixture is stirred at 0° C for 2 hours. The solution is then made basic with 5% aqueous sodium bicarbonate and extracted with ether. The combined extracts are dried over magnesium sulfate and concentrated in vacuo.

The above residue is dissolved in 250 ml of glacial acetic acid, one equivalent of concentrated hydrochloric acid is added, and the resulting solution is hydrogenated in the presence of 5g of 10% palladium/charcoal at 50-60 psi. After uptake of one equivalent of hydrogen, the catalyst is filtered off and the filtrate is concentrated in vacuo to yield the title compound.

EXAMPLE 6

8-[3-[(1,1-Dimethylethyl)amino]-2-hydroxypropoxy]-3a,9a-trans-3a,4,9,9a-tetrahydro-2,2-dimethylnaphtho[2,3-d]-1,3-dioxol-5-ol Following the procedure of Example 1, but substituting dry glacial acetic acid for the solution of glacial acetic acid and water in part (a), yields the title compound.

EXAMPLE 7 trans-4-[3-[(1,1-Dimethylethyl)amino]-2-hydroxypropoxy]-5,6,7,8-tetrahydro-1,6,7-naphthalenetriol, hydrochloride (1:1)

Following the procedure of Example 2, but substituting 8-[3-[(1,1-Dimethylethyl)amino]-2-hydroxypropoxy]-3a,9a-trans-3a,4,9,9a-tetrahydro-2,2-dimethylnaphtho[2,3-d]-1,3-dioxol-5-ol for its cis isomer, yields the title compound.

EXAMPLE 8 trans-4-[2-(Acetyloxy)-3-[(1,1-dimethylethyl)amino]-propoxy]-5,6,7,8-tetrahydro-1,6,7-naphthalenetriol, triacetate ester, hydrochloride (1:1)

Following the procedure of Example 3, but substituting trans-4-[3-[(1,1-dimethylethyl)amino]-2-hydroxypropoxy]-5,6,7,8-tetrahydro-1,6,7-naphthalenetriol, hydrochloride (1:1) for its cis isomer, yields the title compound.

EXAMPLE 9 trans-4-[3-[(1,1-Dimethylethyl)amino]-2-hydroxypropoxy]-5,6,7,8-tetrahydro-1,6,7-naphthalenetriol, 1-acetate Following the procedure of Example 4, but substituting trans-8-[3-[(1,1-Dimethylethyl)amino]-2-hydroxypropoxy]-3a,4,9,9a-tetrahydro-2,2-dimethylnaphtho[2,3-d]-1,3-dioxol-5-ol for its cis isomer yields the title compound.

EXAMPLE 10 trans-4-[2-(Acetyloxy)-3-[(1,1-Dimethylethyl)amino]-propoxy]-5,6,7,8-tetrahydro-1,6,7-naphthalenetriol, 1-acetate Following the procedure of Example 5, but substituting trans-8-[2,3-(epoxy)propoxy]-3a,4,9,9a-tetrahydro-2,2-dimethylnaphtho[2,3-d]-1,3-dioxol-5-ol for its cis isomer, yields the title compound.

EXAMPLES 11–13

Following the procedure of Example 3, but substituting the compound listed in column I for acetyl chloride, yields the compound listed in column II.

|     | Column I | Column II |
| --- | --- | --- |
| 11. | lauryl chloride | cis-4-[3-[(1,1-dimethylethyl-amino]-2-(lauryloxy)propoxy]-5,6,7,8-tetrahydro-1,6,7-naphthalenetriol, trilaurate ester, hydrochloride |
| 12. | o-toluyl chloride | cis-4-[3-[(1,1-dimethylethyl)-amino]-2-(o-toluyloxy)propoxy]-5,6,7,8-tetrahydro-1,6,7-naphth- |

-continued

| | Column I | Column II |
|---|---|---|
| 13. | Phenylacetyl chloride | alenetriol, tri(o-toluate) ester, hydrochloride cis-4-[3-[(1,1-dimethylethyl)-amino]-2-(phenylacetyloxy)propoxy]-5,6,7,8-tetrahydro-1,6,7-naphthalenetriol, tri(phenylacetate) ester, hydrochloride |

EXAMPLES 14–17

Following the procedure of Example 4, but substituting the compound listed in column I for acetic anhydride, yields the compound listed in column II.

| | Column I | Column II |
|---|---|---|
| 14. | isobutric anhydride | cis-4-[3-[(1,1-dimethylethyl)-amino]-2-hydroxypropoxy]-5,6,7,8-tetrahydro-1,6,7-naphthalenetriol, 1-isobutyrate |
| 15. | benzoic anhydride | cis-4-[3-[(1,1-dimethylethyl)-amino]-2-hydroxypropoxy]-5,6,7,8-tetrahydro-1,6,7-naphthalenetriol, 1-benzoate |
| 16. | p-nitrobenzoic anhydride | cis-4-[3-[(1,1-dimethylethyl)-amino]-2-hydroxypropoxy]-5,6,7,8-tetrahydro-1,6,7-naphthalenetriol, 1-(p-nitrobenzoate) |
| 17. | 3-(p-chlorophenyl)-butanoic anhydride | cis-4-[3-[(1,1-dimethylethyl)-amino]-2-hydroxypropoxy]-5,6,7,8-tetrahydro-1,6,7-naphthalenetriol, 1-[3-(p-chlorophenyl)-butanoate] |

EXAMPLES 18–19

Following the procedures of Examples 1 and 2, but substituting the compound listed in column I for t-butylamine, yields the compound listed in column II.

| | Column I | Column II |
|---|---|---|
| 18. | isopropylamine | cis-4-[2-hydroxy-3-(isopropylamino)propoxy]-5,6,7,8-tetrahydro-1,6,7-naphthalenetriol, hydrochloride |
| 19. | methylamine | cis-4-[2-hydroxy-3-(methylamino)-propoxy]-5,6,7,8-tetrahydro-1,6,-7-naphthalenetriol, hydrochloride |

What is claimed is:
1. A compound having the formula

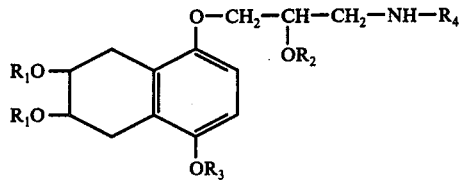

or a pharmaceutically acceptable salt thereof, wherein $R_1$, $R_2$ and $R_3$ are acyl, $R_1$ is hydrogen and $R_2$ and $R_3$ are acyl, or $R_1$ and $R_2$ are hydrogen and $R_3$ is acyl; and $R_4$ is lower alkyl; with the proviso that if more than one of $R_1$, $R_2$ and $R_3$ are acyl, they are the same acyl group; wherein acyl is

wherein X is alkyl having 1 to 11 carbon atoms, aryl, or aryl-lower alkyl; lower alkyl is alkyl of 1 to 4 carbon atoms; and aryl is phenyl or phenyl substituted with one or two lower alkyl, lower alkoxy, halogen or nitro groups.

2. A compound in accordance with claim 1 wherein the —$OR_1$ groups are in the cis configuration.

3. A compound in accordance with claim 1 wherein the —$OR_1$ groups are in the trans configuration.

4. A compound in accordance with claim 1 wherein $R_1$, $R_2$ and $R_3$ are acyl.

5. A compound in accordance with claim 1 wherein $R_1$ is hydrogen and $R_2$ and $R_3$ are acyl.

6. A compound in accordance with claim 1 wherein $R_1$ and $R_2$ are hydrogen and $R_3$ is acyl.

7. A compound in accordance with claim 1 wherein $R_4$ is t-butyl.

8. The compound in accordance with claim 1 having the name cis-4-[2-(acetyloxy)-3-[(1,1-dimethylethyl)amino]propoxy]-5,6,7,8-tetrahydro-1,6,7-naphthalenetriol, triacetate ester, hydrochloride (1:1).

9. The compound in accordance with claim 1 having the name cis-4-[3-[(1,1-dimethylethyl)amino]-2-hydroxypropoxy]-5,6,7,8-tetrahydro-1,6,7-naphthalenetriol, 1-acetate.

10. The compound in accordance with claim 1 having the name cis-4-[2-(acetyloxy)-3-[(1,1-dimethylethyl)amino]propoxy]-5,6,7,8-tetrahydro-1,6,7-naphthalenetriol, 1-acetate.

* * * * *

UNITED STATES PATENT AND TRADEMARK OFFICE
CERTIFICATE OF CORRECTION

PATENT NO. : 4,093,814

DATED : June 6, 1978

INVENTOR(S) : Frederic P. Hauck et al

It is certified that error appears in the above–identified patent and that said Letters Patent are hereby corrected as shown below:

In column 8, Examples 11-13, Column II, No. 11 "dimethylethyl-" should read --dimethylethyl)- --

In column 9, Examples 14-17, Column I, No. 14 "isobutric" should read --isobutyric--

Signed and Sealed this

Twenty-first Day of November 1978

[SEAL]

Attest:

RUTH C. MASON
Attesting Officer

DONALD W. BANNER
Commissioner of Patents and Trademarks